US009095298B2

(12) United States Patent
Ashcraft et al.

(10) Patent No.: US 9,095,298 B2
(45) Date of Patent: Aug. 4, 2015

(54) ADJUSTABLE DISPLAY MECHANISM AND METHOD

(75) Inventors: Danny Ashcraft, Vista, CA (US); Eric Allen, Vista, CA (US); James P. Tenger, Carlsbad, CA (US); John R. Hooks, Carlsbad, CA (US)

(73) Assignee: Intubrite, LLC, Vista, CA (US)

( * ) Notice: Subject to any disclaimer, the term of this patent is extended or adjusted under 35 U.S.C. 154(b) by 351 days.

(21) Appl. No.: 13/593,387

(22) Filed: Aug. 23, 2012

(65) Prior Publication Data

US 2012/0316398 A1 Dec. 13, 2012

Related U.S. Application Data

(63) Continuation-in-part of application No. 13/328,499, filed on Dec. 16, 2011, which is a continuation-in-part of application No. 13/290,792, filed on Nov. 7, 2011, now abandoned, which is a continuation of application (Continued)

(51) Int. Cl.
*A61B 1/267* (2006.01)
*A61B 1/00* (2006.01)
(52) U.S. Cl.
CPC ............ *A61B 1/267* (2013.01); *A61B 1/00048* (2013.01); *A61B 1/00052* (2013.01)
(58) Field of Classification Search
CPC . A61B 1/267; A61B 1/00048; A61B 1/00052
USPC .................................. 600/184–200
See application file for complete search history.

(56) References Cited

U.S. PATENT DOCUMENTS

| D185,398 | S | 6/1959 | Todt |
| 2,946,857 | A * | 7/1960 | Burton ........................ 379/369 |
| 3,863,627 | A | 2/1975 | Bouffard |
| 3,976,054 | A | 8/1976 | Evans |
| 4,380,790 | A | 4/1983 | Saferstein et al. |
| D271,135 | S | 10/1983 | Greenblatt |
| D297,363 | S | 8/1988 | Salerno et al. |
| 4,782,819 | A | 11/1988 | Adair |
| 4,827,910 | A | 5/1989 | Mathews, III |
| 5,165,387 | A | 11/1992 | Woodson |

(Continued)

FOREIGN PATENT DOCUMENTS

KR  1020070044379  4/2007
WO  WO93/01170  6/1993

OTHER PUBLICATIONS

Notification, International Search Report and Written Opinion dated Feb. 8, 2013 from PCT/US2012/63972.

(Continued)

*Primary Examiner* — Eduardo C Robert
*Assistant Examiner* — Stuart S Bray
(74) *Attorney, Agent, or Firm* — Stephen C. Beuerle; Procopio Cory Hargreaves & Savitch LLP

(57) ABSTRACT

A laryngoscope includes a laryngoscope blade; a laryngoscope handle coupled to the laryngoscope blade; an electronic display; and an adjustable display mechanism that adjustably couples the electronic display to the laryngoscope handle. The adjustable display mechanism provides relative rotation of the electronic display relative to the laryngoscope handle about a first axis and a separate second axis different than the first axis.

19 Claims, 5 Drawing Sheets

Related U.S. Application Data

No. 12/698,467, filed on Feb. 2, 2010, now Pat. No. 8,152,719, which is a continuation-in-part of application No. 29/346,594, filed on Nov. 3, 2009, now Pat. No. Des. 632,787, and a continuation-in-part of application No. 12/368,952, filed on Feb. 10, 2009, now abandoned, which is a continuation-in-part of application No. 12/173,961, filed on Jul. 16, 2008, now Pat. No. 8,012,087, which is a continuation-in-part of application No. 12/144,147, filed on Jun. 23, 2008, now Pat. No. 8,257,250.

(60) Provisional application No. 61/288,779, filed on Dec. 21, 2009.

(56) References Cited

U.S. PATENT DOCUMENTS

| | | | |
|---|---|---|---|
| D337,384 S | 7/1993 | Schucman | |
| 5,363,838 A * | 11/1994 | George | 600/120 |
| 5,645,116 A | 7/1997 | McDonald | |
| 5,707,135 A | 1/1998 | Miller, Jr. | |
| 5,812,188 A * | 9/1998 | Adair | 348/77 |
| 5,868,775 A | 2/1999 | Bircoll | |
| 6,095,972 A * | 8/2000 | Sakamoto | 600/190 |
| 6,100,634 A * | 8/2000 | Scholz | 313/490 |
| D449,499 S | 10/2001 | Voges | |
| 6,459,919 B1 | 10/2002 | Lys et al. | |
| 6,466,432 B1 * | 10/2002 | Beger | 361/679.06 |
| 6,569,089 B1 | 5/2003 | Covington et al. | |
| 6,623,425 B2 * | 9/2003 | Cartledge et al. | 600/195 |
| 6,639,789 B2 * | 10/2003 | Beger | 606/46 |
| 6,652,453 B2 * | 11/2003 | Smith et al. | 600/188 |
| D491,267 S | 6/2004 | Ashraf | |
| 6,809,499 B2 | 10/2004 | Solingen | |
| 6,876,446 B2 | 4/2005 | Taylor et al. | |
| D512,778 S | 12/2005 | Ashraf | |
| 6,974,239 B2 | 12/2005 | Currie et al. | |
| 7,052,456 B2 | 5/2006 | Simon | |
| D541,937 S | 5/2007 | Yee | |
| 7,234,204 B2 * | 6/2007 | Liu et al. | 16/367 |
| D547,449 S | 7/2007 | Ashraf | |
| D550,841 S | 9/2007 | Berci et al. | |
| D554,255 S | 10/2007 | Iqbal | |
| 7,308,296 B2 | 12/2007 | Lys et al. | |
| D559,982 S | 1/2008 | Iqbal | |
| D581,532 S | 11/2008 | Cranton et al. | |
| 7,824,331 B1 | 11/2010 | Cranton et al. | |
| 7,946,981 B1 * | 5/2011 | Cubb | 600/194 |
| D641,871 S * | 7/2011 | Tenger et al. | D24/133 |
| 8,257,250 B2 * | 9/2012 | Tenger et al. | 600/199 |
| 8,827,899 B2 * | 9/2014 | Farr et al. | 600/188 |
| 2002/0022769 A1 * | 2/2002 | Smith et al. | 600/188 |
| 2002/0080571 A1 * | 6/2002 | Beger | 361/683 |
| 2002/0087050 A1 * | 7/2002 | Rudischhauser et al. | 600/199 |
| 2002/0089589 A1 * | 7/2002 | Adair et al. | 348/158 |
| 2002/0118279 A1 * | 8/2002 | Spoonhower et al. | 348/66 |
| 2003/0121521 A1 | 7/2003 | Hipolito et al. | |
| 2003/0191459 A1 | 10/2003 | Ganz et al. | |
| 2003/0195390 A1 * | 10/2003 | Graumann | 600/188 |
| 2004/0039252 A1 | 2/2004 | Koch | |
| 2004/0114034 A1 * | 6/2004 | Squilla et al. | 348/66 |
| 2004/0150989 A1 | 8/2004 | Burke et al. | |
| 2004/0240204 A1 | 12/2004 | Russ et al. | |
| 2005/0054903 A1 | 3/2005 | Cantrell | |
| 2005/0159649 A1 | 7/2005 | Patel | |
| 2005/0171399 A1 * | 8/2005 | Rich et al. | 600/112 |
| 2005/0246741 A1 * | 11/2005 | Liu et al. | 725/50 |
| 2006/0030880 A1 | 2/2006 | Tylke | |
| 2006/0069314 A1 | 3/2006 | Farr | |
| 2006/0183978 A1 * | 8/2006 | Howard | 600/197 |
| 2006/0241347 A1 | 10/2006 | Whitehead | |
| 2007/0112257 A1 | 5/2007 | Hensler | |
| 2007/0156022 A1 * | 7/2007 | Patel | 600/199 |
| 2007/0173697 A1 * | 7/2007 | Dutcher et al. | 600/188 |
| 2007/0183145 A1 | 8/2007 | Yu | |
| 2007/0232862 A1 | 10/2007 | Herman | |
| 2007/0276185 A1 * | 11/2007 | Gono et al. | 600/156 |
| 2007/0276191 A1 | 11/2007 | Selover et al. | |
| 2007/0287961 A1 | 12/2007 | Parker | |
| 2008/0015560 A1 | 1/2008 | Gowda et al. | |
| 2008/0045800 A2 | 2/2008 | Mina Farr | |
| 2008/0045801 A1 | 2/2008 | Shalman et al. | |
| 2008/0195128 A1 * | 8/2008 | Orbay et al. | 606/170 |
| 2008/0208006 A1 * | 8/2008 | Farr | 600/178 |
| 2008/0218998 A1 | 9/2008 | Quest et al. | |
| 2008/0300475 A1 | 12/2008 | Jaeger et al. | |
| 2008/0312507 A1 * | 12/2008 | Kim | 600/188 |
| 2009/0076334 A1 | 3/2009 | Chen | |
| 2009/0187078 A1 | 7/2009 | Dunlop | |
| 2009/0270684 A1 * | 10/2009 | Nielsen et al. | 600/193 |
| 2009/0318758 A1 * | 12/2009 | Farr et al. | 600/112 |
| 2010/0095969 A1 * | 4/2010 | Schwartz et al. | 128/207.14 |
| 2010/0152541 A1 * | 6/2010 | Tenger et al. | 600/194 |
| 2010/0249496 A1 * | 9/2010 | Cardenas et al. | 600/104 |
| 2010/0249513 A1 * | 9/2010 | Tydlaska | 600/186 |
| 2011/0009694 A1 * | 1/2011 | Schultz et al. | 600/109 |
| 2011/0028790 A1 * | 2/2011 | Farr et al. | 600/187 |
| 2011/0130627 A1 * | 6/2011 | McGrail et al. | 600/109 |
| 2011/0208002 A1 * | 8/2011 | Kishioka | 600/146 |
| 2011/0270038 A1 * | 11/2011 | Jiang et al. | 600/188 |
| 2012/0209067 A1 * | 8/2012 | Hosaka et al. | 600/109 |
| 2012/0215069 A1 * | 8/2012 | Bullard | 600/188 |
| 2013/0237763 A1 * | 9/2013 | Qiu | 600/188 |
| 2013/0317300 A1 * | 11/2013 | Berci et al. | 600/188 |
| 2014/0288371 A1 * | 9/2014 | Nakatate | 600/156 |

OTHER PUBLICATIONS

International Search Report and Written Opinion for PCT/US08/074878 dated Mar. 19, 2009, 10 pages.

International Search Report and Written Opinion for PCT/US2010/023194 dated Oct. 5, 2010, 8 pages.

ISO 21348, Space Environment (natural and artificial)—Process for determining solar irradiances, 2007, ISO 21348:2007(E).

Walsh, Laurence J. and Shakibaie, Fardad, Ultraviolet-induced fluorescence: shedding new light on dental biofilms and dental carries, Nov./Dec. 2007, Australasian Dental Practice, pp. 56-58.

* cited by examiner

US 9,095,298 B2

ADJUSTABLE DISPLAY MECHANISM AND METHOD

CROSS-REFERENCE TO RELATED APPLICATIONS

This application is a continuation-in-part of U.S. patent application Ser. No. 13/328,499, filed on Dec. 16, 2011, which is a continuation-in-part of U.S. patent application Ser. No. 13/290,792, filed on Nov. 7, 2011, which is a continuation of U.S. patent application Ser. No. 12/698,467, filed Feb. 2, 2010, which is a continuation-in-part of U.S. patent application Ser. No. 29/346,594, filed Nov. 3, 2009, now U.S. Des. Pat. No. D632,787, and is a continuation-in-part of U.S. patent application Ser. No. 12/368,952, filed Feb. 10, 2009, now abandoned, which is a continuation-in-part of U.S. patent application Ser. No. 12/173,961, filed on Jul. 16, 2008, now U.S. Pat. No. 8,012,087, which is a continuation-in-part of U.S. patent application Ser. No. 12/144,147, filed Jun. 23, 2008. This application also claims priority under 35 U.S.C. 119(e) to U.S. Provisional Patent Application No. 61/288,779, filed Dec. 21, 2009. The contents of each and all of the above patent applications are incorporated herein by reference in their entirety.

FIELD OF THE INVENTION

The field of this invention relates to display mechanisms for laryngoscopes and the laryngoscopy procedure.

SUMMARY OF THE INVENTION

An aspect of the invention involves an adjustable display mechanism that couples a laryngoscopy electronic display to a laryngoscope intubation handle. The adjustable display mechanism allows the display to rotate in two dimensions and prevents binding or breaking of the electrical wires within the connectors and electronic display. The display is allowed to rotate in the vertical axis between zero and 90 degrees and may be locked in place once adjusted to the desired angle. Enough friction is provided in this axis such that the rotation need not be locked while still holding the desired position. The display is allowed to rotate in the horizontal axis 180 degrees in either direction with stops at the end of this rotation. Further, the display's rotation provides tactile feedback at several locking points, providing for incremental movement without locking down the rotation in this axis.

Another aspect of the invention involves a laryngoscope including a laryngoscope blade; a laryngoscope handle coupled to the laryngoscope blade; an electronic display; and an adjustable display mechanism that adjustably couples the electronic display to the laryngoscope handle. The adjustable display mechanism provides relative rotation of the electronic display relative to the laryngoscope handle about a first axis and a separate second axis different than the first axis.

One or more implementations of the aspect of the invention described immediately above includes one or more of the following: the adjustable display mechanism includes a fixed sleeve coupled to the laryngoscope handle and a top rotatably coupled to the fixed sleeve for rotation relative to the fixed sleeve about the first axis; the adjustable display mechanism includes a pivot for rotatably coupling the electronic display to the top for rotation relative to the top about the second axis; the relative rotation about the first axis is between 0 degrees and 180 degrees relative rotation about the first axis; the relative rotation about the second axis is between 0 degrees and 90 degrees relative rotation about the second axis; a pull connector couples the adjustable display mechanism to the laryngoscope handle; and/or the pivot is lockable to lock the electronic display in a fixed position relative to the top.

A further aspect of the invention involves an adjustable display mechanism for adjustably coupling an electronic display to a laryngoscope handle of a laryngoscope. The adjustable display mechanism includes a fixed sleeve coupleable to the laryngoscope handle; and a top rotatably coupled to the fixed sleeve for providing relative rotation of the electronic display relative to the laryngoscope handle about a first axis and including a pivot for providing relative rotation of the electronic display relative to the laryngoscope handle about a separate second axis different than the first axis.

One or more implementations of the aspect of the invention described immediately above includes one or more of the following: the relative rotation about the first axis is between 0 degrees and 180 degrees relative rotation about the first axis; the relative rotation about the second axis is between 0 degrees and 90 degrees relative rotation about the second axis; a pull connector for couples the adjustable display mechanism to the laryngoscope handle; the pivot is lockable to lock the electronic display in a fixed position relative to the laryngoscope handle; and/or a method of using the adjustable display mechanism of comprising rotatably coupling the top of the fixed sleeve to the electronic display; coupling the fixed sleeve to the laryngoscope handle; rotating the electronic display relative to the laryngoscope handle about the first axis; rotating the electronic display relative to the laryngoscope handle about the separate second axis different than the first axis; viewing the electronic display while performing laryngoscopy.

Further objects and advantages will be apparent to those skilled in the art after a review of the drawings and the detailed description of the preferred embodiments set forth below.

DETAILED DESCRIPTION OF PREFERRED EMBODIMENTS

Figure 1:
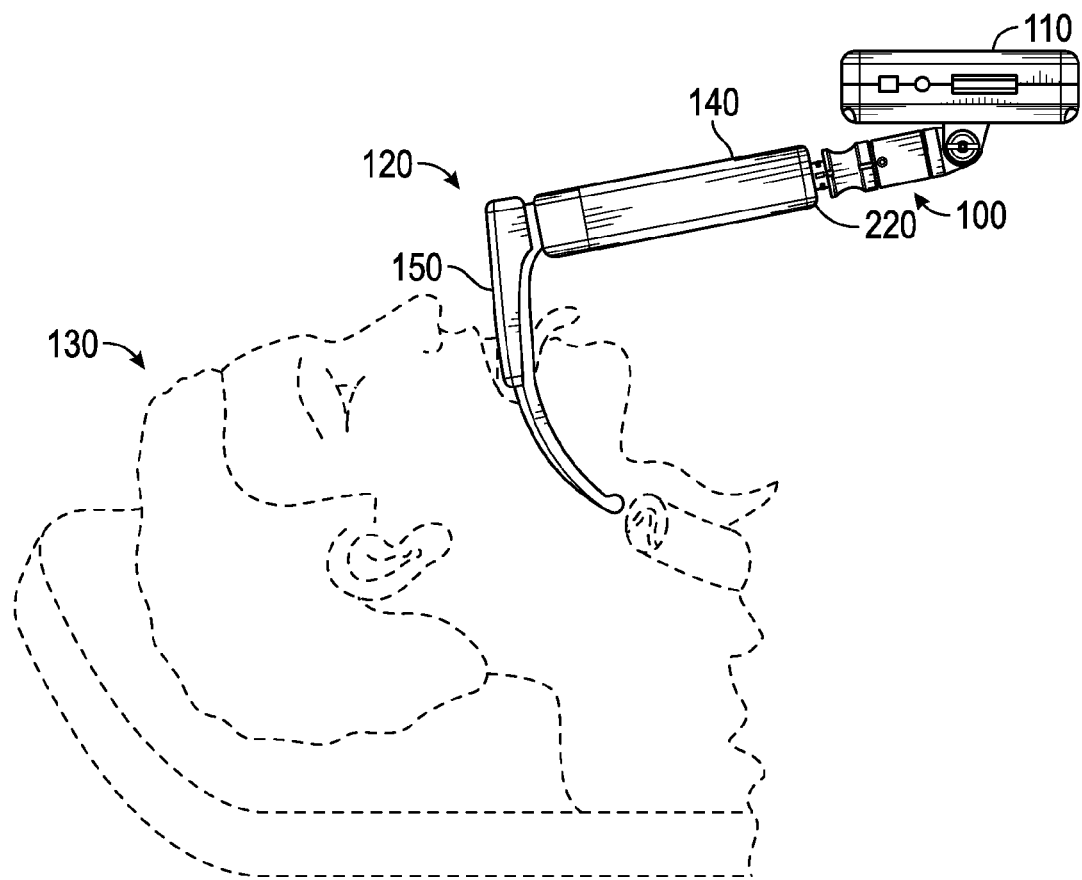
FIG. 1 is a schematic depiction of a laryngoscope being used with an embodiment of an adjustable display mechanism and an electronic display to view a patient's larynx.

With reference to FIGS. 1-5, an embodiment of an adjustable display mechanism 100 that adjustably couples an electronic display 110 to a laryngoscope 120 will be described. In FIG. 1, the laryngoscope 120 is shown placed in the mouth of a patient 130 for viewing the vocal cords adjacent the larynx and to aid in the insertion of an endotracheal tube past the vocal cords or aid in the removal of a foreign object. The laryngoscope 120 includes a handle 140 and a blade portion 150, the latter being used to lift the tongue and mandible out of the way for viewing the vocal cords. Although the adjustable display mechanism 100 will be shown and described in conjunction with an electronic display for a laryngoscope, in alternative embodiments, the adjustable display mechanism 100 is used for adjustably coupling a display to other medical devices other than a laryngoscope for medical procedures other than laryngoscopy.

The adjustable display mechanism 100 includes an attachment device flange 160 at a first end that pivotally connects to display flanges or tilt ears 170 extending from a rear 175 of the electronic display 110 via a lock pin 180. The flanges 160, 170 and pin 180 forming a pivot for allowing rotation of the electronic display 110 about pivot axis 190 between 0 degrees and 90 degrees relative to adjustable display mechanism 100 and handle 140. The lock pin 180 allows the electronic display 110 to be locked in place once adjusted to the desired angle. The adjustable display mechanism 100 includes a pull connector 200 at an opposite second end that is used to connect connection shaft 210 to a receiving end 220 of laryngoscope handle 140. The pull connector 200 includes a pull sleeve 205 that is slidably disposed along the connection shaft 210 and is coupled to fixed sleeve 230 via dowel pin 240. The connection shaft 210 is received with a receiving hole 250 of the fixed sleeve 230. The fixed sleeve 230 includes a shaft 260 extending through the fixed sleeve 230 and into a top 270. Circumferentially surrounding the shaft 260 in the fixed sleeve 230 are O-rings 280. Circumferentially surrounding the shaft 260 in the top 270 is stop ring 285, which includes stops for providing 180 degree rotation of the top 270 relative to the fixed sleeve 230 about longitudinal axis 290. The shaft 260 is connected to the top via dowel pin 300.

The adjustable display mechanism 100 will now be described in use. The adjustable display mechanism 100 is connected to the electronic display 110 by removing the lock pin 180, positioning the attachment device flange 160 between the tilt ears 170 on the rear 175 of the electronic display 110, and replacing the lock pin 180 so that the electronic display 110 is pivotally coupled to the adjustable display mechanism 100 at its first end. The electronic display 110 and the adjustable display mechanism 100 are connected to the laryngoscope handle 140 by slidably engaging pull sleeve 205, inserting the connection shaft 210 into the receiving end 220 of laryngoscope handle 140, and releasing the pull sleeve 205. This locks the connection shaft 210 to the receiving end 220 of the laryngoscope handle 140.

The adjustable display mechanism 100 allows the electronic display 110 to rotate in two dimensions.

Figure 2:
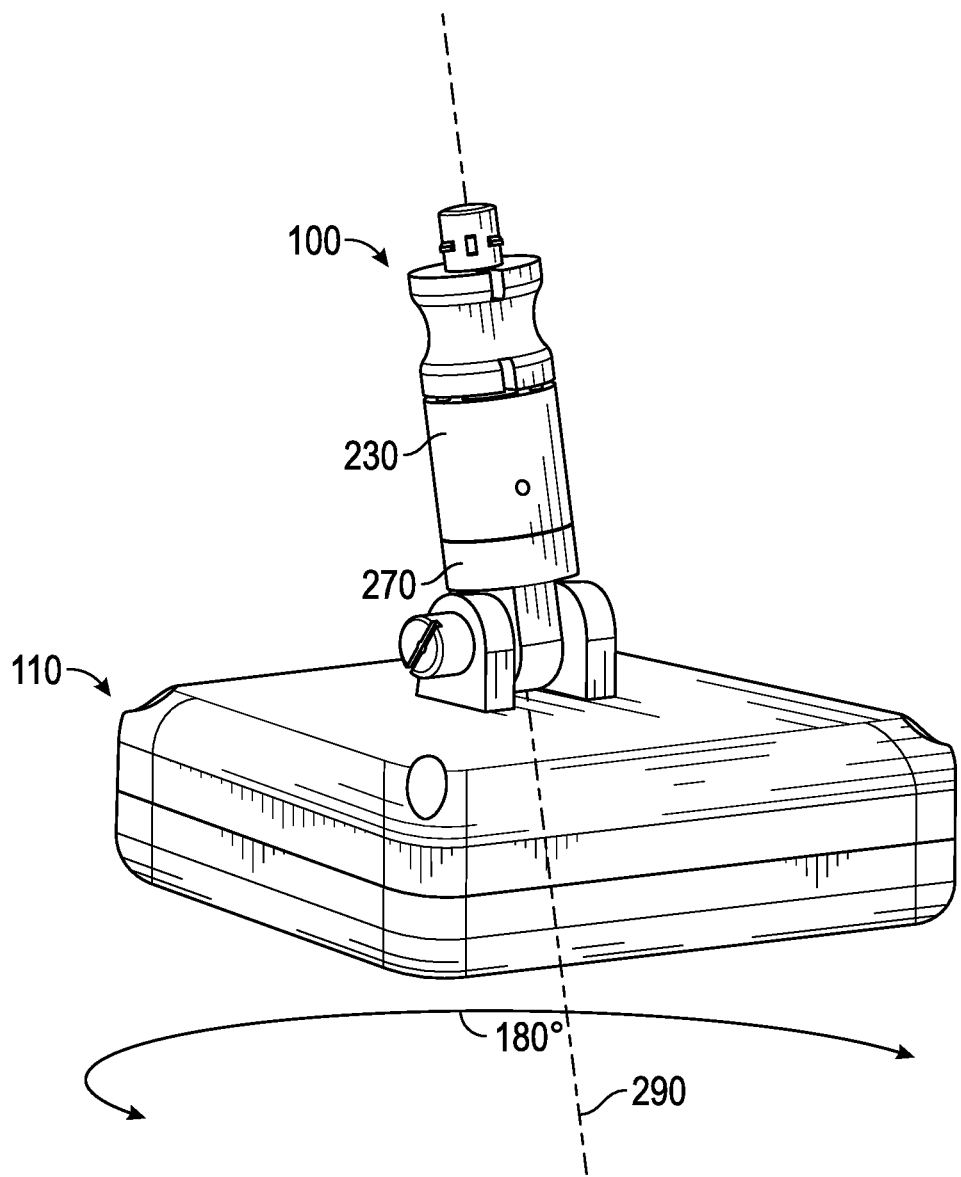
FIG. 2 is a perspective view of the adjustable display mechanism and the electronic display, showing how the display is allowed to rotate in the horizontal axis 180 degrees in either direction.
Figure 3:
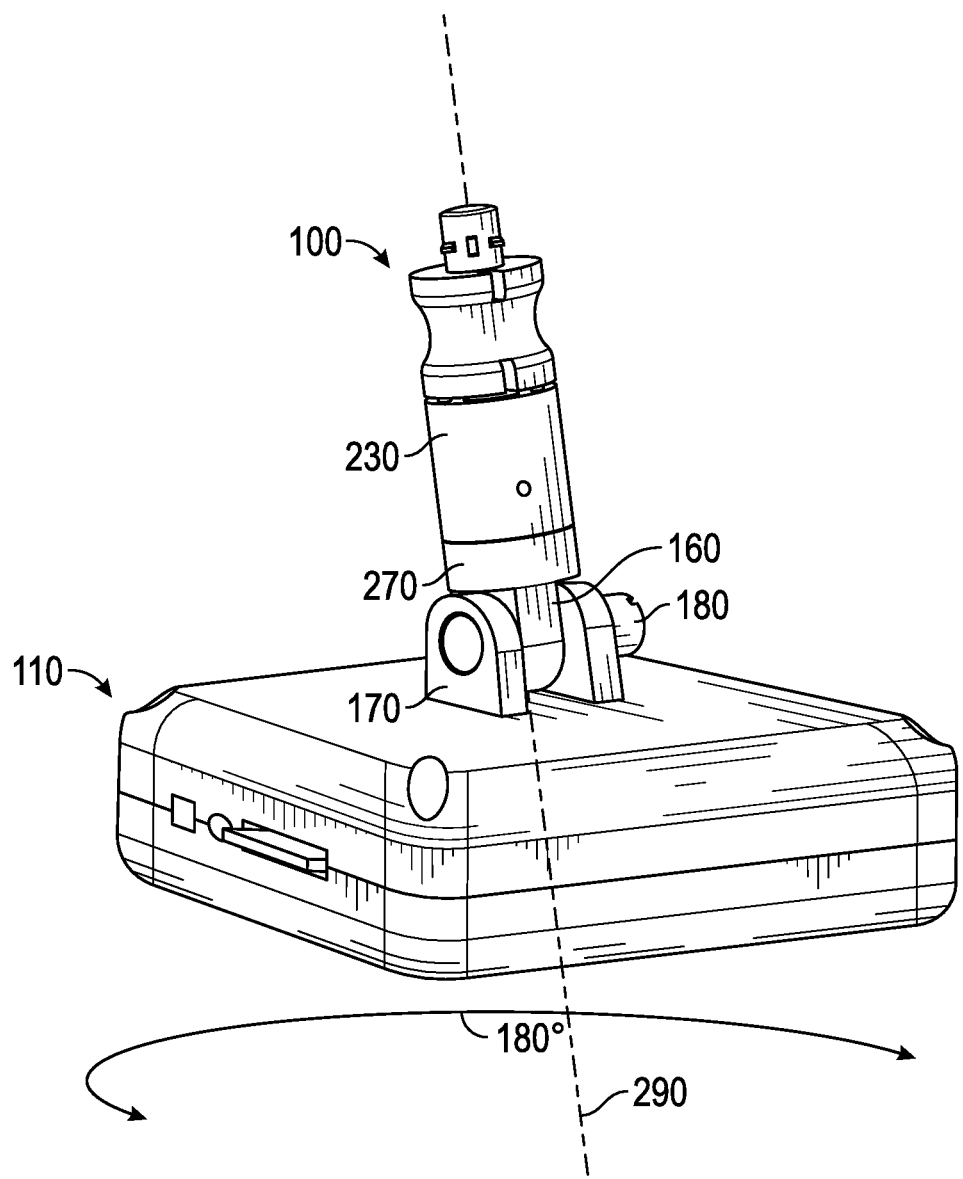
FIG. 3 is another perspective view of the adjustable display mechanism and the electronic display, showing how the display is allowed to rotate in the horizontal axis 180 degrees in either direction.

With reference to FIGS. 2 and 3, the top 270 and the electronic display 110 rotate 180 degrees relative to the fixed sleeve 230 about axis 290. The electronic display is allowed to rotate about the axis 290 180 degrees in either direction with stops at the end of this rotation. Further, the electronic display's rotation provides tactile feedback at several locking points, providing for incremental movement without locking down the rotation in this axis 290.

Figure 4:
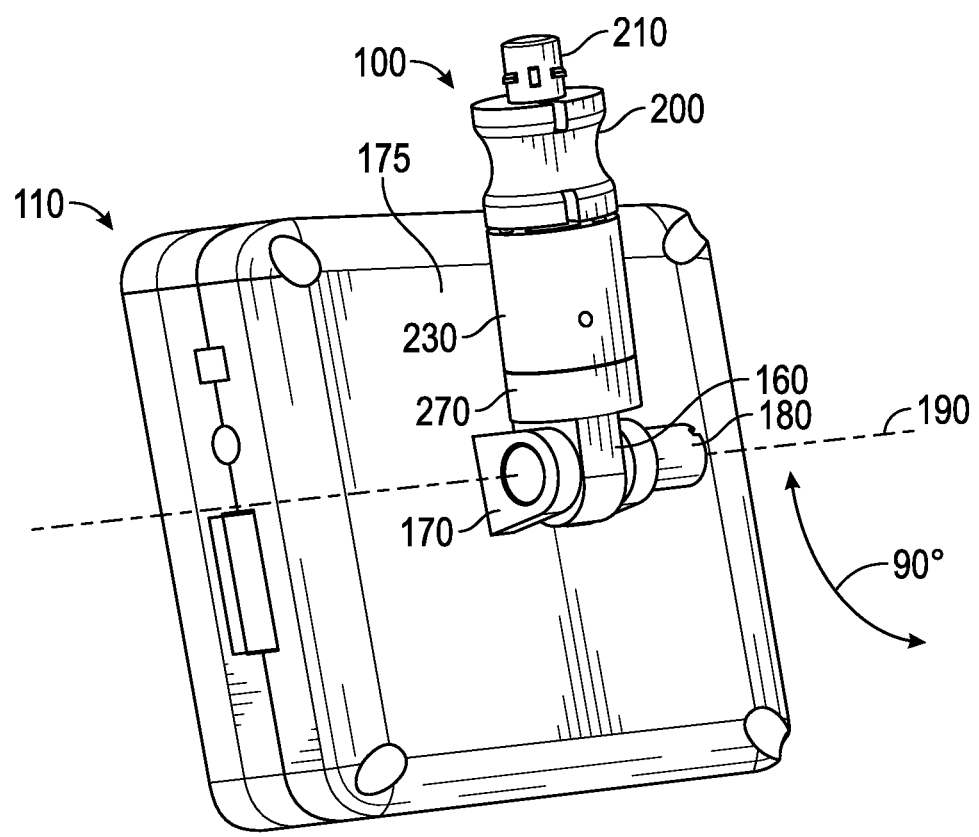
FIG. 4 is a perspective view of the adjustable display mechanism and the electronic display, showing how the display is allowed to rotate in the vertical axis between zero and 90 degrees.
Figure 5:
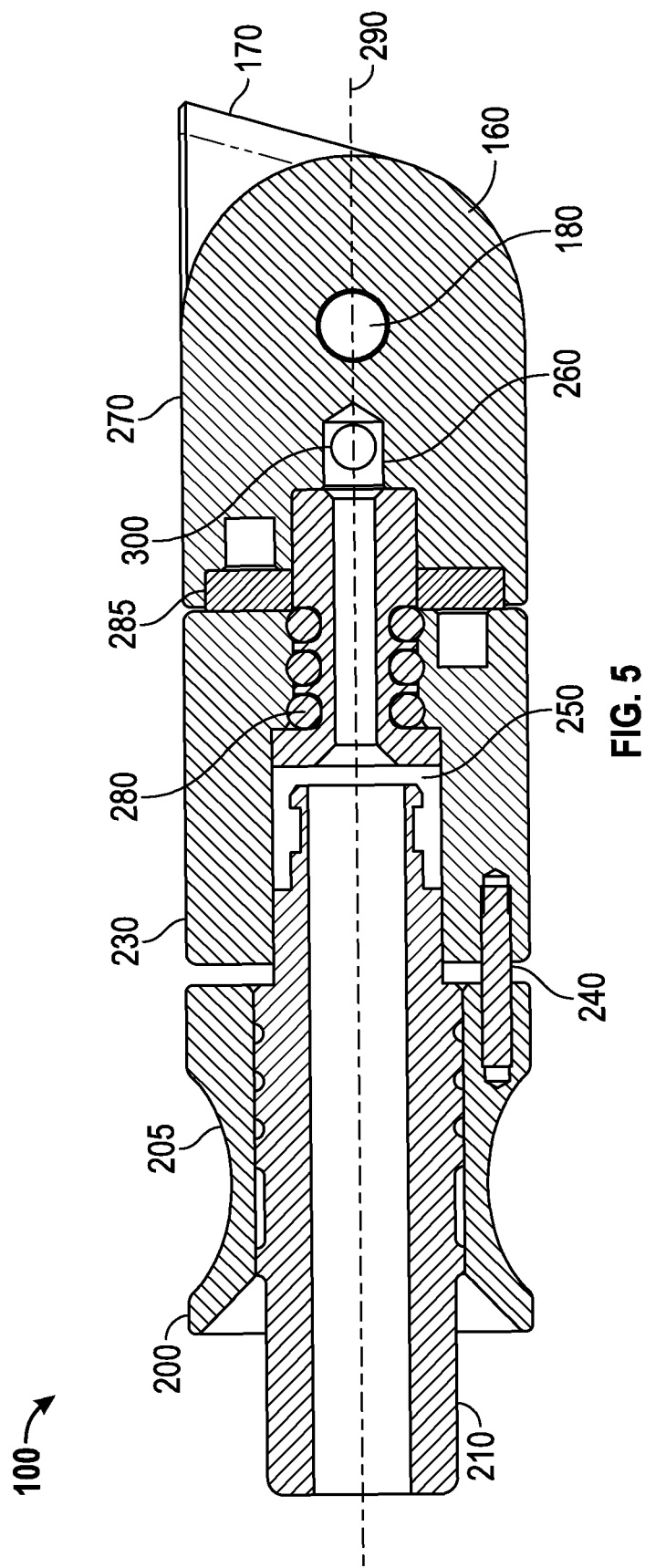
FIG. 5 is a cross-sectional view of the adjustable display mechanism.

With reference to FIG. 4, the tilt ears 170 and the electronic display 110 rotate 90 degrees relative to the attachment device flange 160 about axis 190. The electronic display 110 may be locked in place with the lock pin 180 once the electronic display 110 is adjusted to the desired angle. Enough friction is provided in this pivot such that the rotation need not be locked while still holding the desired position.

Once the electronic display 110 is in the desired position, the electronic display 110 is viewed while performing laryngoscopy with the laryngoscope 120.

The adjustable display mechanism 100 has electrical wires running through the adjustable display mechanism 100 for electrically coupling the laryngoscope handle 140 to the electronic display 110. The adjustable display mechanism 100 prevents binding or breaking of the electrical wires within the adjustable display mechanism 100 and the electronic display 110.

The above figures may depict exemplary configurations for the invention, which is done to aid in understanding the features and functionality that can be included in the invention. The invention is not restricted to the illustrated architectures or configurations, but can be implemented using a variety of alternative architectures and configurations. Additionally, although the invention is described above in terms of various exemplary embodiments and implementations, it should be understood that the various features and functionality described in one or more of the individual embodiments with which they are described, but instead can be applied, alone or in some combination, to one or more of the other embodiments of the invention, whether or not such embodiments are described and whether or not such features are presented as being a part of a described embodiment. Thus the breadth and scope of the present invention, especially in the following claims, should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; and adjectives such as "conventional," "traditional," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, a group of items linked with the conjunction "and" should not be read as requiring that each and every one of those items e present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

We claim:

1. A laryngoscope, comprising:
a laryngoscope blade;
a laryngoscope handle coupled to the laryngoscope blade;
an electronic display;
an adjustable display mechanism that adjustably couples the electronic display to the laryngoscope handle, the adjustable display mechanism providing relative rotation of the electronic display relative to the laryngoscope handle about a first axis and a separate second axis different than the first axis,
wherein the adjustable display mechanism includes a fixed sleeve coupled to the laryngoscope handle, a top rotatably coupled to the fixed sleeve for rotation relative to the fixed sleeve about the first axis, a pull connector slidably movable with respect to fixed sleeve and coupling the adjustable display mechanism to the laryngoscope handle.

2. The laryngoscope of claim 1, wherein the pull connector includes a pull sleeve.

3. The laryngoscope of claim 2, wherein the laryngoscope handle includes a receiving end, the adjustable display mechanism includes a connection shaft that is received by the receiving end of the laryngoscope handle, and the pull connector is used to connect the connection shaft to the receiving end of the laryngoscope handle.

4. The laryngoscope of claim 3, wherein the adjustable display mechanism includes a dowel pin and the pull sleeve is slidably disposed along the connection shaft and is coupled to fixed sleeve via the dowel pin.

5. The laryngoscope of claim 4, wherein the fixed sleeve includes a receiving hole and the connection shaft is received with the receiving hole of the fixed sleeve.

6. The laryngoscope of claim 5, wherein the adjustable display mechanism includes a top and the fixed sleeve includes a shaft extending through the fixed sleeve and into the top.

7. The laryngoscope of claim 6, further including a stop ring circumferentially surrounding the shaft in the top, the stop ring including stops for providing 180 degree rotation about the first axis in either direction, preventing binding or breaking of electrical wires within the adjustable display mechanism.

8. The laryngoscope of claim 1, wherein the adjustable display mechanism includes a pivot for rotatably coupling the electronic display to the top for rotation relative to the top about the second axis.

9. The laryngoscope of claim 8, wherein the relative rotation about the second axis is between 0 degrees and 90 degrees relative rotation about the second axis.

10. The laryngoscope of claim 8, wherein the pivot is lockable to lock the electronic display in a fixed position relative to the top.

11. The laryngoscope of claim 1, wherein the relative rotation about the first axis is between 0 degrees and 180 degrees relative rotation about the first axis.

12. The laryngoscope of claim 1, wherein the laryngoscope handle and the adjustable display mechanism are coaxial.

13. The laryngoscope of claim 1, wherein the electronic display includes a rear and the adjustable display mechanism adjustably couples the rear of the electronic display to the laryngoscope handle.

14. The laryngoscope of claim 1, wherein the adjustable display mechanism includes several locking points, providing tactile feedback at the locking points and incremental movement without locking down the rotation.

15. An adjustable display mechanism for adjustably coupling an electronic display to a laryngoscope handle of a laryngoscope, comprising:
a fixed sleeve coupleable to the laryngoscope handle; and
a top rotatably coupled to the fixed sleeve for providing relative rotation of the electronic display relative to the laryngoscope handle about a first axis and including a pivot for providing relative rotation of the electronic display relative to the laryngoscope handle about a separate second axis different than the first axis,
wherein the adjustable display mechanism includes a fixed sleeve coupled to the laryngoscope handle, a top rotatably coupled to the fixed sleeve for rotation relative to the fixed sleeve about the first axis, a pull connector slidably movable with respect to fixed sleeve and coupling the adjustable display mechanism to the laryngoscope handle.

16. The laryngoscope of claim 15, wherein the relative rotation about the first axis is between 0 degrees and 180 degrees relative rotation about the first axis.

17. The laryngoscope of claim 15, wherein the relative rotation about the second axis is between 0 degrees and 90 degrees relative rotation about the second axis.

18. The laryngoscope of claim 15, wherein the pivot is lockable to lock the electronic display in a fixed position relative to the laryngoscope handle.

19. A method of using the adjustable display mechanism of claim 15, comprising:
rotatably coupling the top of the fixed sleeve to the electronic display;
coupling the fixed sleeve to the laryngoscope handle;
rotating the electronic display relative to the laryngoscope handle about the first axis;
rotating the electronic display relative to the laryngoscope handle about the separate second axis different than the first axis;
viewing the electronic display while performing laryngoscopy.

* * * * *